US006928375B2

(12) United States Patent
Ono et al.

(10) Patent No.: US 6,928,375 B2
(45) Date of Patent: Aug. 9, 2005

(54) INSPECTION CONDITION SETTING PROGRAM, INSPECTION DEVICE AND INSPECTION SYSTEM

(75) Inventors: Makoto Ono, Yokohama (JP); Yohei Asakawa, Yokohama (JP); Hisafumi Iwata, Hayama (JP); Kanako Harada, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/411,785

(22) Filed: Apr. 10, 2003

(65) Prior Publication Data

US 2003/0195712 A1 Oct. 16, 2003

(30) Foreign Application Priority Data

Apr. 10, 2002 (JP) .................................. 2002-107284

(51) Int. Cl.[7] ............................................. G06F 19/00
(52) U.S. Cl. ............................................. 702/81; 702/84
(58) Field of Search ....................... 250/306, 307, 250/309, 310; 382/141, 144, 145, 149, 190, 195, 147, 151; 356/237.1, 237.2, 237.3, 237.4, 237.5, 237.6, 451, 601; 700/95, 96, 108, 109, 110; 702/81, 83, 84, 127

(56) References Cited

U.S. PATENT DOCUMENTS

| | | | | |
|---|---|---|---|---|
| 3,751,647 A | * | 8/1973 | Maeder et al. | ............... 713/401 |
| 5,173,719 A | | 12/1992 | Taniguchi et al. | |
| 5,233,191 A | * | 8/1993 | Noguchi et al. | ............ 250/306 |
| 5,663,569 A | | 9/1997 | Hayano | ................. 250/559.45 |
| 5,754,432 A | | 5/1998 | Komatsuzaki et al. | |
| 5,867,389 A | * | 2/1999 | Hamada et al. | ............. 700/121 |
| 5,936,710 A | * | 8/1999 | Itoh et al. | ...................... 355/53 |
| 6,028,991 A | * | 2/2000 | Akashi | ......................... 716/14 |
| 6,099,581 A | * | 8/2000 | Sakai | .......................... 716/11 |
| 6,185,474 B1 | * | 2/2001 | Nakamura et al. | .......... 700/121 |

(Continued)

FOREIGN PATENT DOCUMENTS

| | | | | |
|---|---|---|---|---|
| GB | 1357859 A | * | 6/1974 | ........... H01L/07/64 |
| JP | 48-40376 | | 6/1973 | |
| JP | 05258015 A | * | 10/1993 | ........... G06F/15/60 |
| JP | 07161787 A | * | 6/1995 | ........... H01L/21/66 |
| JP | 08162510 A | * | 6/1996 | ........... H01L/21/66 |

OTHER PUBLICATIONS

Yasutsugu Usami, et al., "Special Edition: Semiconductor Manufacturing/Inspection Systems Opening Up the Era of 0.1 μm Devices," 662 *Hitachi Review* (Oct. 1999), 81(10):51–56.

(Continued)

*Primary Examiner*—John Barlow
*Assistant Examiner*—Douglas N. Washburn
(74) *Attorney, Agent, or Firm*—Townsend and Townsend and Crew LLP

(57) ABSTRACT

A program is provided for setting efficiently, and with precision, the inspection conditions of an inspection device that detects particles and deformed patterns in or on products such as semiconductor integrated circuits that are manufactured by simultaneously forming a plurality of products on a single substrate. In particular, the system achieves greater efficiency of the setting of cell comparison regions and the setting of non-inspection regions. Input processing of a product type code, input processing of chip size and configuration information, reading processing of circuit layout data, extraction processing of repeated pattern region coordinates, extraction processing of sparse region coordinates and circuit pattern condition registration processing are sequentially executed.

14 Claims, 9 Drawing Sheets

U.S. PATENT DOCUMENTS

| | | | | |
|---|---|---|---|---|
| 6,263,477 B1 | * | 7/2001 | Kobayashi | 716/5 |
| 6,285,783 B1 | * | 9/2001 | Isomura et al. | 382/147 |
| 6,289,493 B1 | * | 9/2001 | Kita | 716/11 |
| 6,320,646 B1 | * | 11/2001 | Mouri | 355/53 |
| 6,347,150 B1 | * | 2/2002 | Hiroi et al. | 382/149 |
| 6,366,688 B1 | * | 4/2002 | Jun et al. | 382/145 |
| 6,410,927 B1 | * | 6/2002 | Pike | 250/491.1 |
| 6,445,441 B1 | * | 9/2002 | Mouri | 355/53 |
| 6,487,472 B1 | * | 11/2002 | Song et al. | 700/121 |
| 6,493,082 B2 | * | 12/2002 | Nara et al. | 356/394 |
| 6,514,345 B1 | * | 2/2003 | Nagata et al. | 118/697 |
| 6,566,654 B1 | * | 5/2003 | Funatsu et al. | 250/310 |
| 6,621,571 B1 | * | 9/2003 | Shishido et al. | 356/237.5 |
| 6,629,051 B2 | * | 9/2003 | Tanaka | 702/81 |
| 6,631,590 B1 | * | 10/2003 | Glowaski | 52/63 |
| 6,674,889 B1 | * | 1/2004 | Takayama | 382/149 |
| 6,687,633 B2 | * | 2/2004 | Ono et al. | 702/83 |
| 6,700,122 B2 | * | 3/2004 | Matsui et al. | 250/310 |
| 2002/0052053 A1 | * | 5/2002 | Ono et al. | 438/12 |
| 2002/0113234 A1 | * | 8/2002 | Okuda et al. | 257/48 |
| 2003/0058436 A1 | * | 3/2003 | Ono et al. | 356/237.2 |
| 2003/0076989 A1 | * | 4/2003 | Maayah et al. | 382/145 |

OTHER PUBLICATIONS

C. H. Stapper, "Modeling of Defects in Integrated Circuit Photolithographic Patterns," *IBM J. Res. Develop,* (Jul. 1984), 28(4):461–475.

* cited by examiner

INSPECTION CONDITION SETTING PROGRAM, INSPECTION DEVICE AND INSPECTION SYSTEM

BACKGROUND OF THE INVENTION

1. Field of the Invention

The present invention relates to an inspection condition setting programs that are executed by inspection devices or inspection systems for products such as semiconductor integrated circuits.

2. Description of the Related Art

The related art is described below using manufacture of semiconductor integrated circuits as an example. The manufacturing processes for integrated circuits are typically divided into wafer patterning processes and packaging processes. In wafer patterning processes, chips are manufactured with formation of multiple layers, such as circuit and interconnection pattern layers, usually on a silicon wafer. In packaging processes, the chips are separated and packaged.

In the wafer pattering processes, disconnections or short-circuits of the circuit patterns may arise because of such defects as particles or deformed patterns generated during manufacture. Un-patterned or patterned wafer inspection devices are employed to monitor defects. An un-patterned wafer inspection device directs a laser beam onto the wafer in inclined fashion from above and the scattered light is detected. The device is sometimes referred to as a "dark field" inspection device. A patterned wafer inspection device detects abnormal locations by picking up images of the circuit patterns and performing image processing thereon. Patterned wafer inspection devices are categorized into "bright field" inspection devices or SEM (Scanning Electron Microscope) inspection devices depending on the detector employed. The article "Inspection System Supporting Improved Semiconductor Yields" in the October 1999 issue of the *Hitachi Journal* describes these devices. However, there is no clear distinction between the un-patterned and patterned wafer inspection devices except the principle of inspection. In the present application, both devices are referred to generally as defect inspection devices.

Defect inspection devices play an important role in high-sensitivity detection of defects on circuit patterns formed on wafers. To make full use of the defect inspection device, it is necessary to set suitable inspection conditions in accordance with the method of deposition onto the wafer and the method of formation of the circuit patterns. Typically, a defect inspection device requires inspection conditions set beforehand to execute inspection programs. Two of the conditions to be set are circuit pattern conditions and optical/image processing conditions.

The circuit pattern conditions include parameters such as the size of the chips that are formed on the wafer, the arrangement information and region information within the inspection algorithm can be changed accordingly. In addition, the optical/image processing conditions determine the inspection sensitivity and include parameters such as the amount of laser illumination that depends on deposition conditions and the wiring material, the contrast condition of images picked up by the detectors, and threshold values in image processing etc. The circuit pattern conditions and optical/image processing conditions are interrelated.

In the circuit pattern conditions, parameters such as size and arrangement of the chips formed on the wafer are the same parameters used in exposure conditions. Since the inspection algorithms can be changed depending on the circuit pattern of the integrated circuit, regions within a chip need to be set for executing the respective algorithms. The inspection algorithms include, for example, chip comparison methods (also called die comparison methods), cell comparison methods and mixed comparisons methods combining chip comparison and cell comparison. Japanese Patent No. 3187827 discloses these methods. Note that in some cases detection sensitivity can be increased by excluding some regions from the defect inspection area. The regions to be excluded are, for example, a region in which no circuit pattern is present, such as the region between one chip and another on the wafer (called the "scribe lines"), or the region between one circuit block and another in a chip. In setting the circuit pattern conditions, such regions are registered as non-inspection regions.

Conventionally, circuit pattern conditions, except the parameters of the size and the arrangement of chips on the wafer, must be determined while observing the surface of the real wafer. To observe the surface of the real wafer, the wafer must be set into the defect inspection device and moved with an XY stage that holds the wafer.

BRIEF SUMMARY OF THE INVENTION

The present invention provides a program whereby the circuit pattern conditions of the defect inspection device can be set rapidly and with high precision. Conventionally, the operator sets up the conditions by mounting an actual wafer in the defect inspection device; the following problems are therefore experienced. (1) Considerable time is taken to set the inspection conditions. In particular, in a production line in which a large number of different types of products were produced in small quantities, the task of setting the inspection conditions must be performed frequently. (2) Differences between operators can affect inspection conditions. In setting non-inspection regions or cell comparison regions using actual wafers, differences between individuals may result in inappropriate inspection conditions being set.

The present invention provides a program to set the circuit pattern conditions of a defect inspection device rapidly and with high precision using circuit layout data prepared by a CAD (Computer Aided Design) system. The program, according to the invention, may be an embodiment in which the program is stored in a secondary storage device of the defect inspection device and read and executed by a primary storage device of the defect inspection device, or an embodiment in which the program is stored in a secondary storage device of another computer separate from the defect inspection device and read and executed by this primary storage device, the output file being utilized by downloading the file to defect inspection devices through a network or removable storage medium.

Specifically, according to the present invention, in a program executed to set inspection conditions of an inspection device that detects the positions of particles and deformed patterns present in the subject of inspection, an inspection condition setting program is provided whereby there is executed circuit layout reading processing in which layout data of a circuit formed on the subject of inspection is read; repeated pattern region coordinate extraction processing in which the coordinates of repeated pattern regions in the circuit layout are extracted from circuit layout data read by this reading processing; and inspection region registration processing in which the coordinates of repeated pattern regions extracted by this extraction processing are registered as inspection regions of the inspection device.

DETAILED DESCRIPTION OF THE INVENTION

Figure 1:
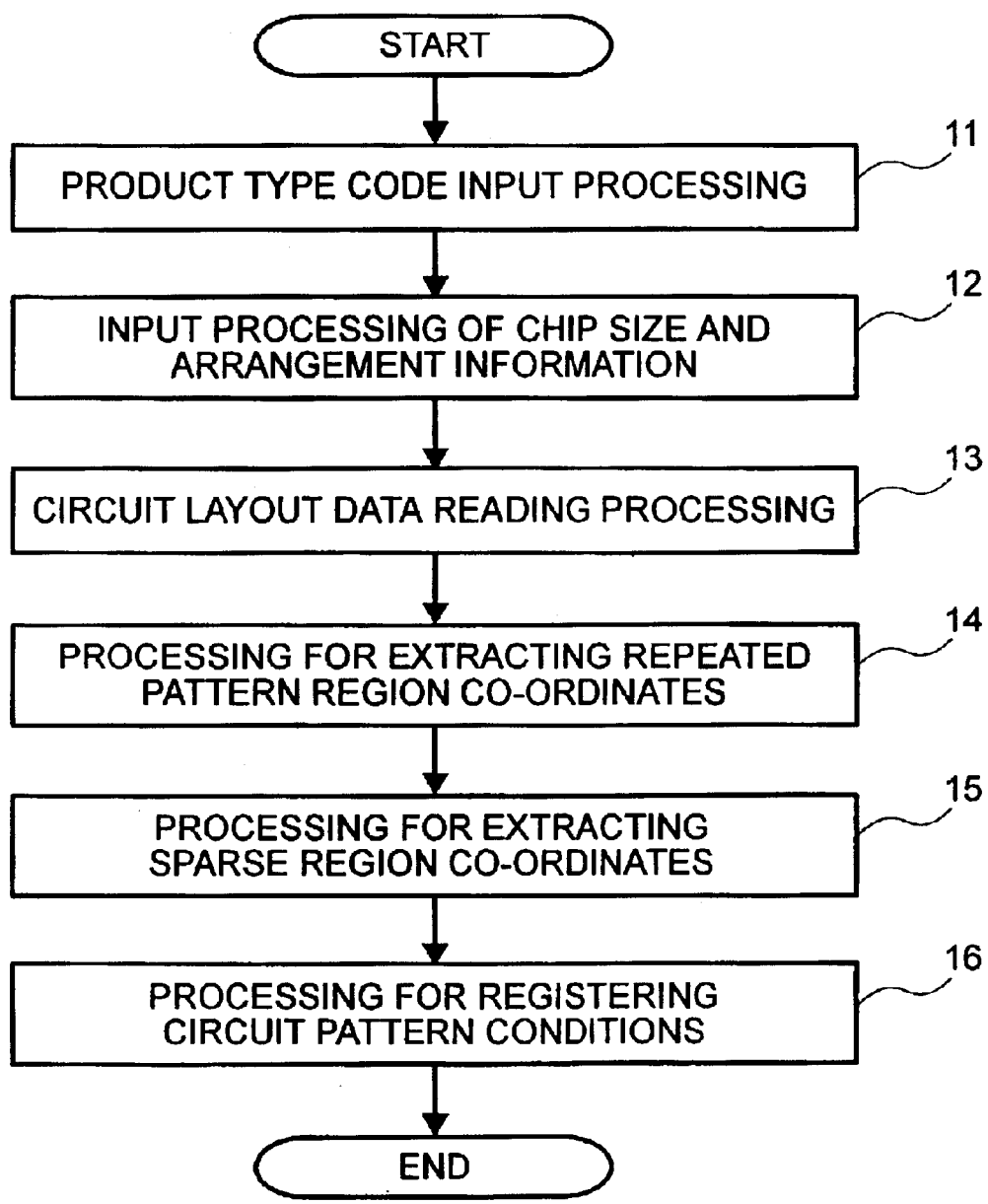
FIG. 1 is a view of an embodiment of a setting procedure for circuit pattern conditions according to the present invention.

An embodiment of the present invention is described with reference to the drawings. FIG. 1 is an example of a processing method for setting circuit pattern conditions of the inspection conditions of a defect inspection device according to the present invention. In FIG. 1, step 11, the product type code is input. The product type code is a code number corresponding to the product type of the integrated circuit formed on the wafer. In step 12, information corresponding to the product type code about chip size and arrangement of the chips is input. More specifically, the following parameters are input: values (called the longitudinal chip pitch) regarding size in the longitudinal transverse directions of the individual chips formed on the wafer, scribe line width and size in the longitudinal direction; values (called the transverse chip pitch) regarding the scribe line width and size in the transverse direction; and the number of chip columns and rows formed on the wafer. If this information is provided beforehand in the form of data on another computer it may be read by downloading through a network.

In step 13, circuit layout data of an integrated circuit corresponding to the product type code is read. The circuit layout data is, for example, the data that is provided for forming the integrated circuits on the wafer by using exposure devices. An integrated circuit has a multilayer structure formed by a plurality of exposures. The circuit layout data therefore includes data for a plurality of layers. In step 14, the coordinates of repeated pattern regions present in the circuit layout data are extracted. Repeated pattern regions are regions in which a large number of transistors of the same shape, contact holes of the same shape, capacitors of the same shape or wiring of the same shape, etc., are provided in matrix fashion. Typical examples are static random access memory sections, flash memory sections, dynamic random access memory sections or read-only memory sections in an integrated circuit chip.

In step 15, the coordinates of sparse regions are extracted. Sparse regions are regions in which the circuit patterns are not densely integrated, such as scribe line regions between one chip and another or the regions between one circuit block and another within a chip where, even if particles or small scratches are produced, there is minimal effect on the viability of the integrated circuits. They are usually designated as non-inspection regions. In step 16, the circuit pattern conditions are registered using the information input or extracted in steps 11 to 15.

Figure 2:
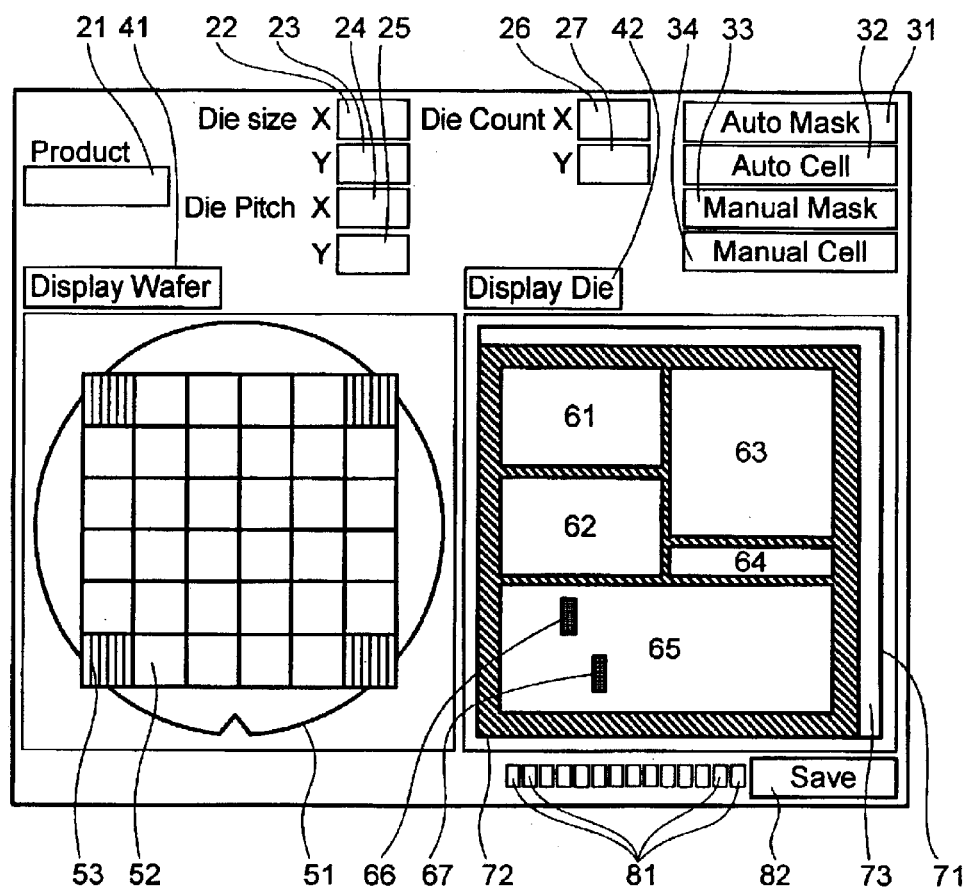
FIG. 2 is a view of an embodiment of a GUI for setting circuit pattern conditions.

FIG. 2 is an example of a GUI (Graphical User Interface) for implementing the present invention. The GUI includes a product type code 21 input area, an input area for chip size in the transverse direction 22, an input area for chip size in the longitudinal direction 23, an input area for chip pitch in the transverse direction 24, an input area for chip pitch in the longitudinal direction 25, an input area for the number of chip rows 26 on the wafer and is an input area for the number of chip columns 27. An execute button 31 is provided for automatically extracting the coordinates of a non-inspection regions, as are a button 33 for changing to a mode for manually altering the coordinates of the non-inspection regions, and a button 34 for changing to a mode for manually altering the coordinates of the repeated pattern regions.

Element 41 is a wafer map display button. Elements 51 and 52 (described below) are drawn by clicking this button with the mouse after inputting product type code 21, chip pitch in the transverse direction 24, chip pitch in the longitudinal direction 25, number of chip rows 26 and number of chip columns 27. Element 51 displays the outer periphery of the wafer and element 52 displays a chip as a single rectangle. In this example the number of chip rows is input as "6" and the number of chip columns is input as "6". The chip arrangement is determined by a change of color 53, by using the mouse to click on chips that are not actually formed or chips that, although formed, are not designated as subjects of inspection. Processing up to this point is that of steps 11 and 12 of FIG. 1. Element 42 is a display button for the circuit layout within a chip. By clicking button 42 with the mouse, the circuit layout data corresponding to the product type code is read and drawn. The circuit layout data prepared by the CAD system is information relating to a single chip and does not include information regarding the scribe lines between the chips. The circuit layout is therefore drawn from the ratios of the values of chip size in the transverse direction 22, chip size in the longitudinal direction 23, chip pitch in the transverse direction 24 and chip pitch in the longitudinal direction 25. Element 71 is the outer frame of the chip pitch and element 72 is the outer frame of a chip. The circuit layout is drawn such that the respective bottom left-hand ends of the outer frame 71 of the chip pitch and the outer frame 72 of the chip coincide. Elements 61 to 65 are examples in which a circuit block within the chip is drawn from the circuit layout data. These examples include, SRAM circuit blocks 61 and 62, a CPU circuit block 63, a ROM circuit block 64, and a logic circuit block 65. The respective circuit blocks are basically independently formed at the stage where the transistors are formed and are connected at the stage where the wiring is formed. The circuit layout data includes information about a plurality of layers. The layer that is displayed can be altered using a plurality of buttons 81.

The coordinates of non-inspection regions are automatically extracted from the circuit layout data by using the mouse to click on an execute button for processing to automatically extract the coordinates of non-inspection regions 31. In this example, scribe line region 73 between outer frame 71 of the chip pitch and outer frame 72 of the chip size is automatically extracted. Scribe line region 73 is an area where the circuit pattern is sparse. Then, a region within the chip, indicated by shading, is automatically extracted. The region, which does not belong to any of the SRAM circuit blocks 61 and 62 or CPU circuit block 63, ROM circuit block 64 or logic circuit block 65, is a region where the circuit pattern is sparse. Elements 66 and 67 are areas that are extracted as sparse regions within a circuit block (the method of extraction is described later). Regions that are extracted as non-inspection regions are displayed in a different color.

After execution of the above automatic extraction processing, the setting on the screen can be altered by using the mouse to click button 33 to change to the mode for manually altering the coordinates of a non-inspection regions. For example, regions that were automatically extracted as non-inspection regions owing to their circuit pattern being sparse can be changed to inspection regions. Regions that were not automatically designated as non-inspection regions owing to their circuit patterns being dense can be changed to non-inspection regions.

The coordinates of repeated pattern regions are automatically extracted by using a mouse to click on execute button 32 for automatically extracting the coordinates of repeated pattern regions. The repeated pattern regions are calculated and set for each layer. The repeated pattern regions for each layer are displayed in a different color. The layer that is displayed is changed using a plurality of buttons 81. The coordinates of the repeated pattern regions that are thus extracted are used as the coordinates for executing cell comparison processing.

After execution of the above automatic extraction processing, the setting on the screen can be changed by using a mouse to click on button 34 for changing to a mode for manually altering the coordinates of repeated pattern regions. In this way, a region that was automatically extracted as a repeated pattern region can be changed to a different pattern region.

By using the mouse to click button 82, the product type code, chip size, chip pitch, arrangement information, repeated pattern region coordinates and sparse region coordinates, are registered as circuit pattern conditions of the inspection conditions. This is step 16 of FIG. 1. In this embodiment, in which the program of the present invention is stored in a secondary storage device of the defect inspection device and is read into a primary storage device of the defect inspection device in order to be executed, these conditions are registered in the secondary storage device in the circuit pattern condition data format characteristic of the defect inspection device, by using a mouse to click button 82. Alternatively, in an embodiment in which the program is stored in a secondary storage device of another computer separate from the defect inspection device and is read into a primary storage device of the computer in order to be executed, these conditions are registered by XL (Extensible Markup Language) or SOAP (Simple Object Access Protocol) by using a mouse to click button 82. The circuit pattern conditions registered by XL or SOAP are downloaded through a network in accordance with the requirements of various types of defect inspection devices and converted into the circuit pattern condition data format characteristic of the defect inspection device being used, and registered in the secondary storage device of the defect inspection device. In this way, compatibility can be achieved by using XL or SOAP, and the registered circuit pattern conditions can be shared by defect inspection devices of different manufacturers.

Figure 3:
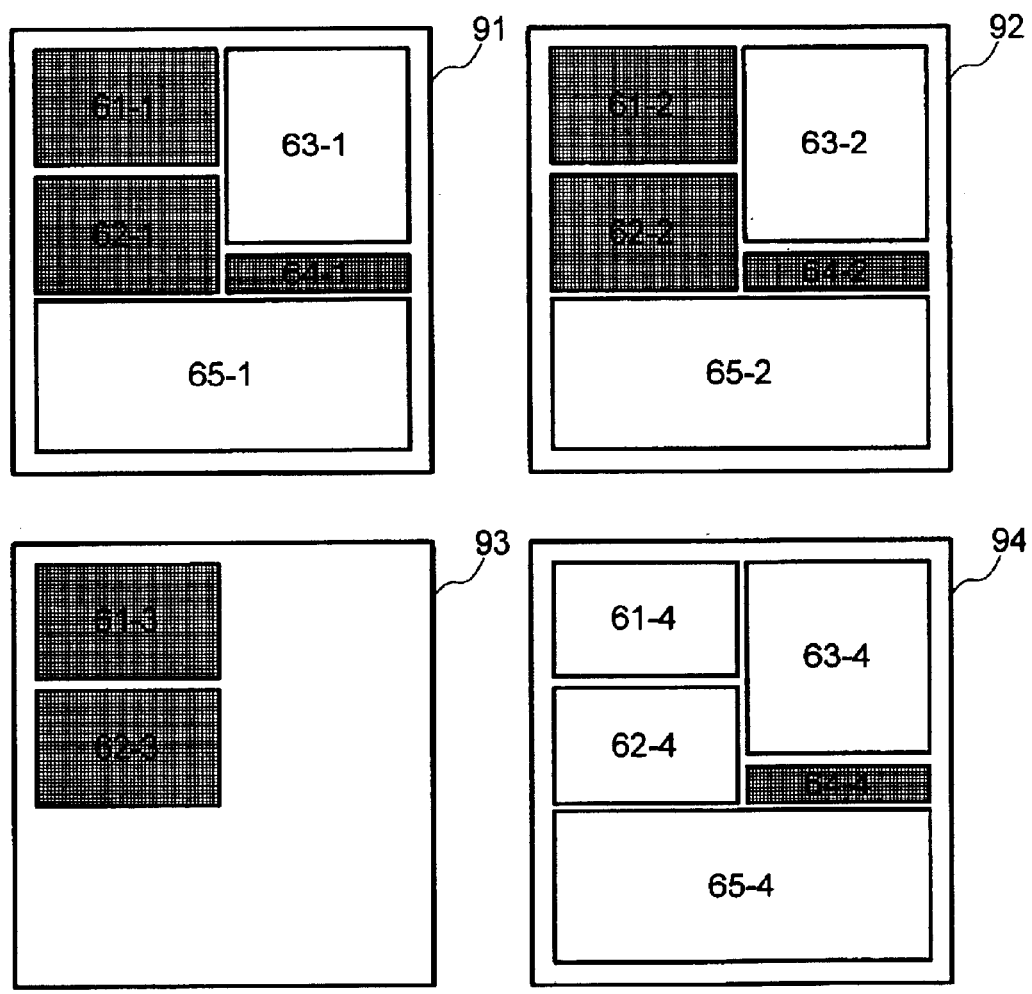
FIG. 3 is an example of the results of extracting repeated pattern regions for each layer.

FIG. 3 shows an example of the results of extracting repeated pattern regions in a chip. Repeated pattern regions are extracted for each layer of a multilayer integrated circuit. In this example, repeated pattern regions are extracted in four layers. Elements 91, 92, 93 and 94 indicate the results of extracting repeated pattern regions for each respective layer; the rectangles of the outer frames are the outer respective frames of the chips. The circuit blocks indicated in gray are extracted as repeated pattern regions. In layer 91, SRAM circuit blocks 61-1 and 61-2 and ROM circuit block 64-1 are extracted as repeated pattern regions. Similarly, in layer 92, SRAM circuit blocks 61-2 and 62-2 and ROM circuit block 64-2 are extracted as repeated pattern regions. In layer 93 only SRAM circuit blocks are present, so SRAM circuit blocks 61-3 and 62-3 are extracted as repeated pattern regions. In layer 94, only ROM circuit block 64-4 is extracted as a repeated pattern region. Thus, even in the case of a memory circuit section, there may be cases where some regions are not extracted as repeated pattern regions. The significance of this is that, even in the case of a memory circuit section, there may be cases, in layers where the wiring are formed where the pattern is not necessarily completely repeated.

Figure 4:
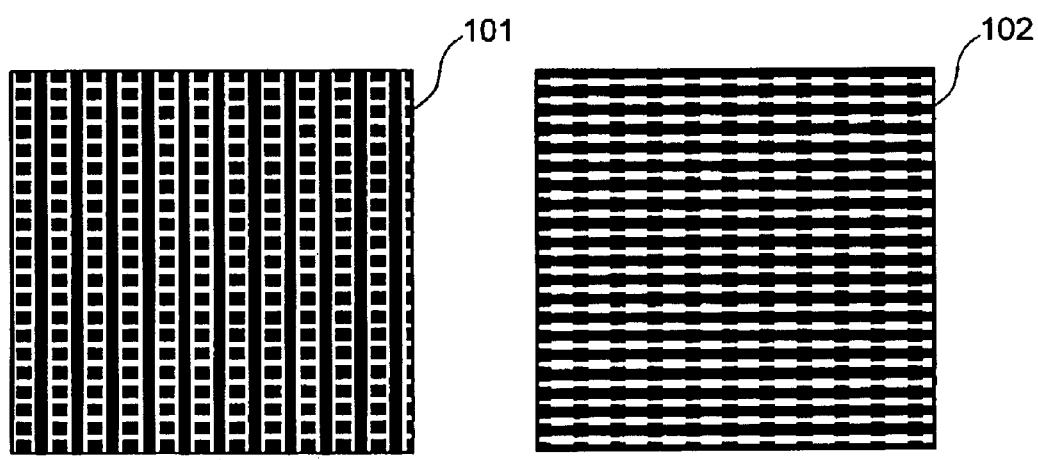
FIG. 4 is an example showing a larger scale of a repeated pattern.

FIG. 4 is an example of a repeated pattern. In this figure, elements 101 and 102 represent repeated patterns at a larger scale at the same locations in different layers. A repeated pattern region is one in which a circuit pattern of the same shape is repeated.

Figure 5:
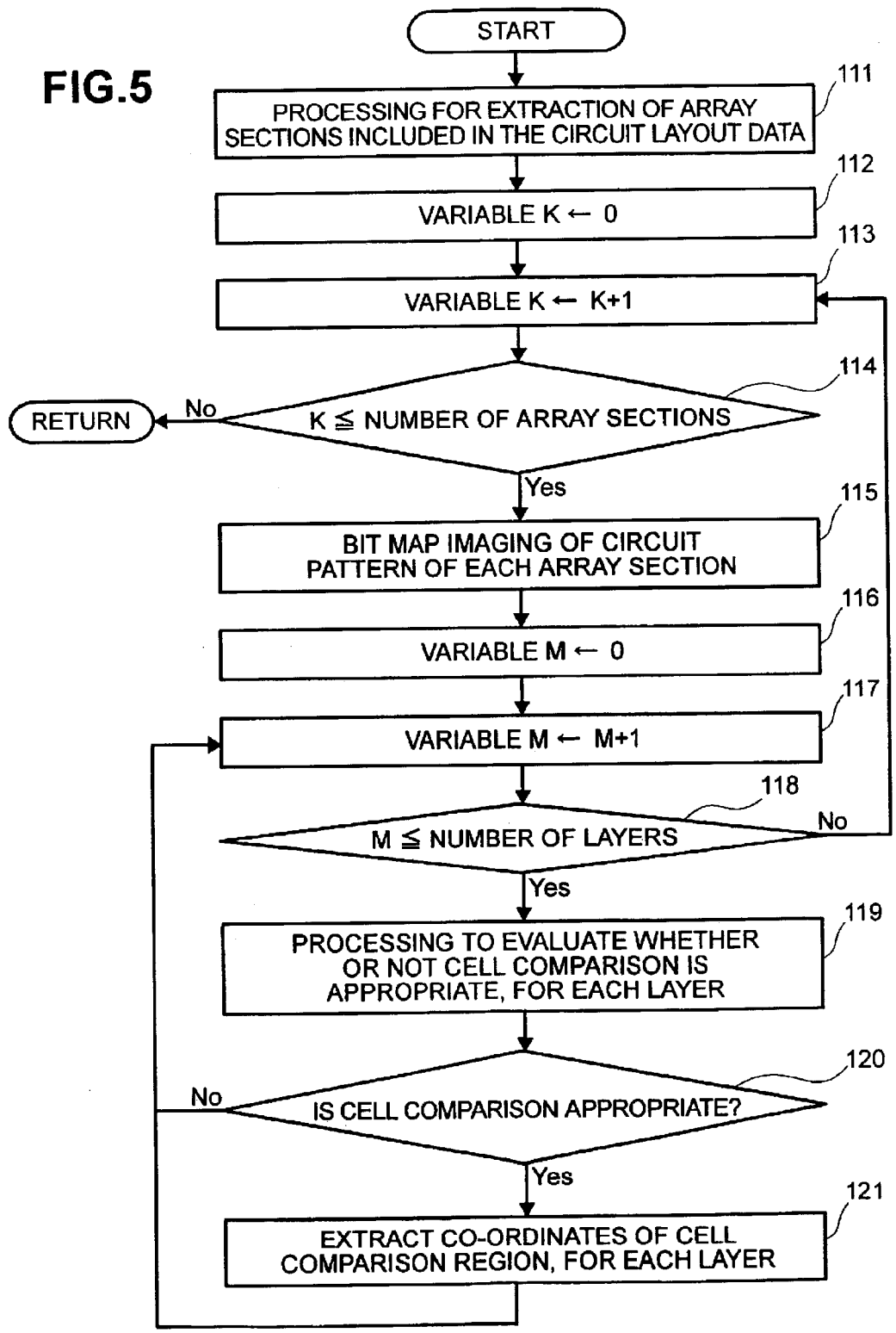
FIG. 5 is an example of a procedure for extracting repeated pattern region coordinates.

FIG. 5 shows an example of the procedure for extracting the coordinates of a repeated pattern region. In step 111, extraction processing of array sections included in the circuit layout data is performed. The array section is a portion having a data structure for forming circuit patterns of the same shape repeated longitudinally and transversely. All the array sections that are present are identified by scanning the circuit layout data. Next, in step 112, variable K is initialized. The value of variable K is the identification number of the individual array sections extracted in step 111. In step 113, variable K is incremented. If, in step 114, variable K is less than or equal to the number of array sections that have been extracted in step 111, processing advances to Yes; if variable K exceeds the number of array sections, processing advances to No. In step 115, the array section corresponding to variable K is loaded into the primary storage device by generating the bit map image data constituting the circuit patterns. In step 116, the variable M is initialized. Variable M is the identification number of a layer of an integrated circuit of having a multi-layered structure. In step 117, variable M is incremented. In step 118, if variable M is less than or equal to the layer number, processing advances to Yes; if variable M exceeds the layer number, processing advances to No. In step 119, an evaluation is conducted regarding whether or not cell comparison is feasible with respect to the circuit patterns of the layer corresponding to variable M. "Evaluation as to whether or not cell comparison is feasible" consists of conducting the same processing as cell comparison processing mounted as a function of the defect inspection device. In the evaluation process, the program uses the bit map image data of the circuit patterns loaded into the primary storage device instead of using the real wafer images detected by the defect inspection device. In contrast to a case where processing is conducted in respect of the image of the real wafer, the bit map image data of the circuit patterns contains no defects. So, even though cell comparison processing is performed with the bit map images, defects (a location that does not coincide with the same location on the adjacent cell) will not be detected. Accordingly, it will be concluded that cell comparison is feasible as long as no defects are detected in cell comparison processing using bit map images. In contrast, during cell comparison processing, if defects (a location that does not coincide with the same location on the adjacent cell) are detected, cell comparison processing will not be possible, so it will be concluded that cell comparison is not feasible. An example of a circuit pattern in which cell comparison is not feasible occurs if the repeated pattern is larger than the image size in image processing in cell comparison processing. In step 120, condition branching is performed based on the results of the evaluation regarding cell comparison feasibility performed in step 119. If cell comparison is feasible, processing advances to Yes; if cell comparison is not feasible, processing advances to No. In step 121, the vertex of the circuit pattern that is the subject of evaluation is extracted as the coordinates of the repeated pattern region of the layer corresponding to variable M. This cell comparison feasibility evaluation processing makes possible setting of the "cell comparison region" for the inspection conditions.

Figure 6:
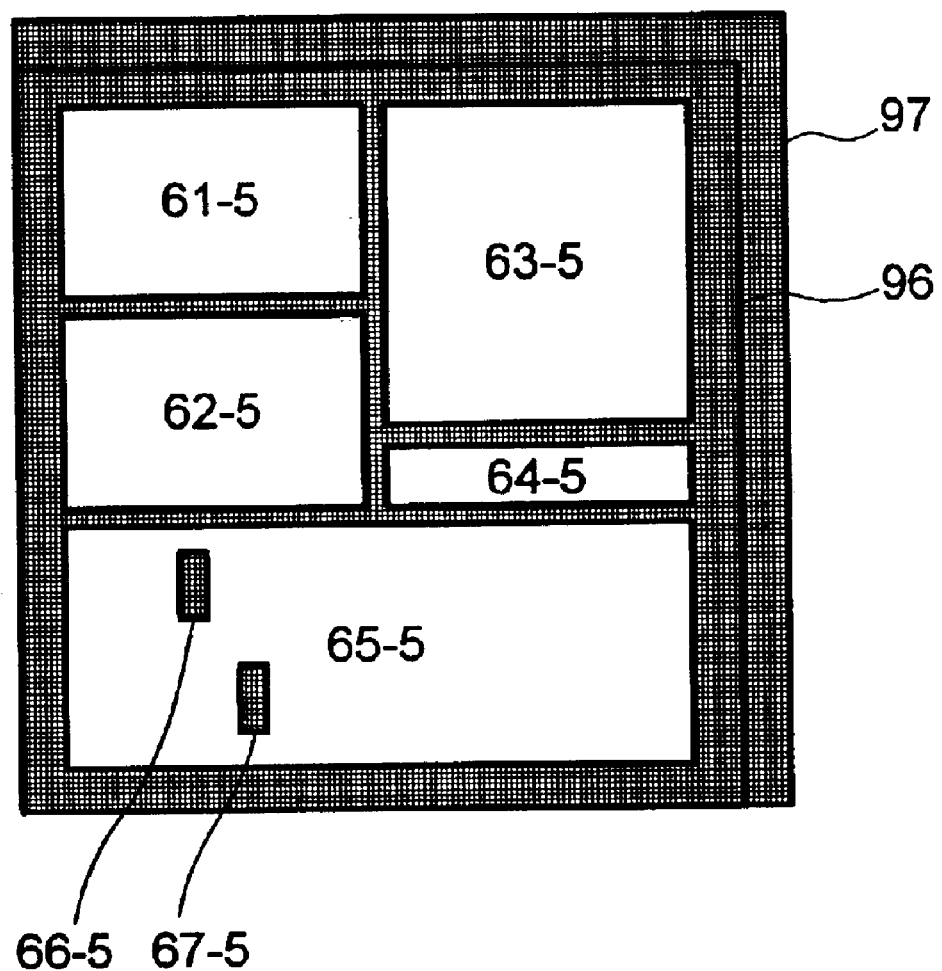
FIG. 6 is an example of the results of extracting non-inspection regions within the chip pitch.

FIG. 6 shows an example of the result of extracting non-inspection regions. Rectangle 97 is the outer frame of the chip pitch and rectangle 96 is the outer frame of the chip. The region indicated in gray is the area extracted as the non-inspection region. Regions which are extracted as non-inspection regions include these regions: regions that are within the chip pitch but are not included in the chip, regions that are within the chip but are not included in any circuit block, and regions 65-5 and 67-5 within logic circuit block 65-5. In general, it is desirable that the same non-inspection regions are set for each layer, so that the results shown in FIG. 6 can be employed in all the layers. However, different settings for each layer would also be possible.

Figure 7:
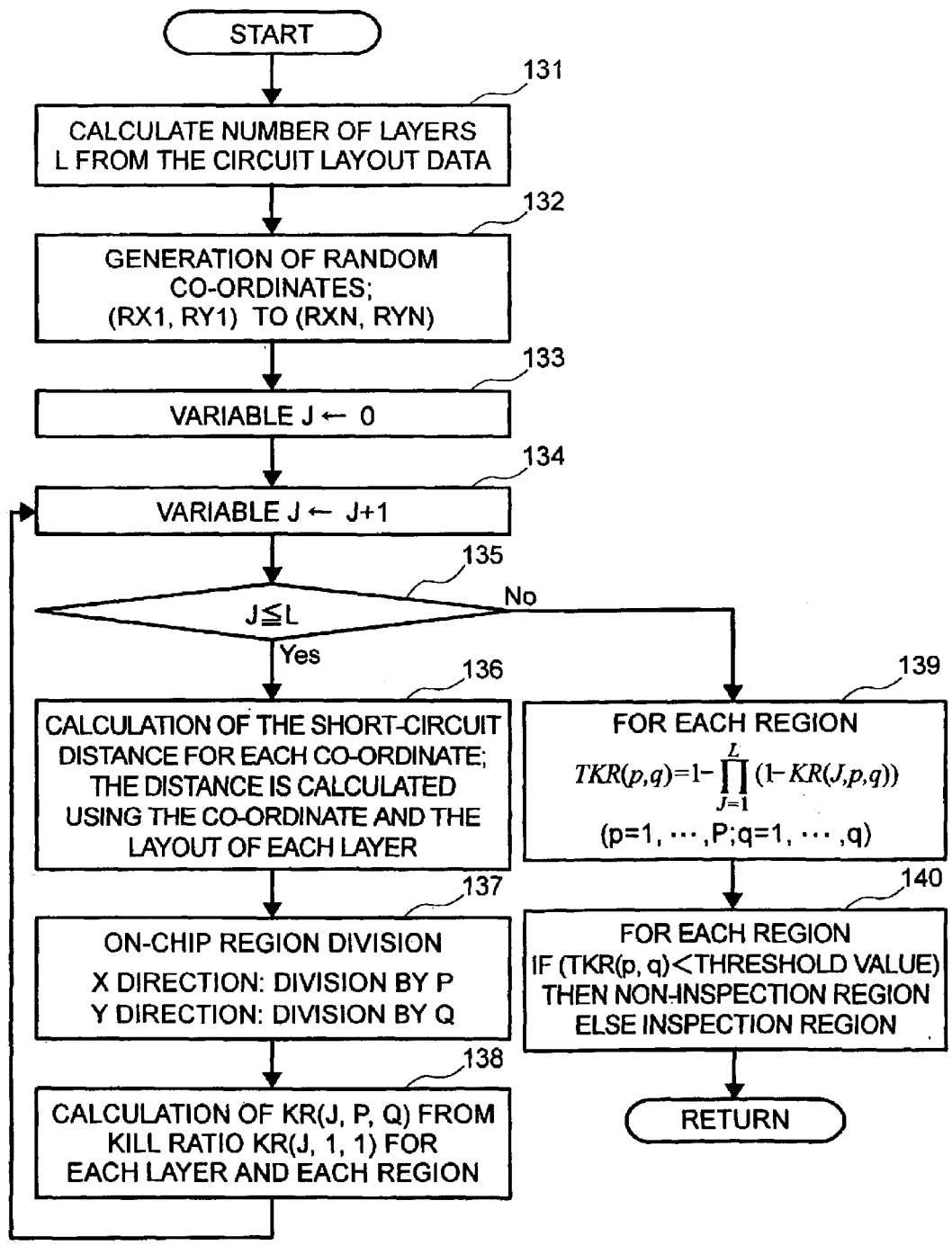
FIG. 7 is an example of a procedure for extracting the coordinates of non-inspection regions within a chip.

FIG. 7 shows an example of a procedure for extracting the coordinates of non-inspection regions. Since extraction of regions that are within the chip pitch but are not included in the chip, i.e. Scribe line regions, is easy, the procedure for extracting the coordinates of non-inspection regions within the chip is now described. In step 131, the circuit layout data is scanned and the number of layers that this circuit layout data has is calculated. This layer number is then inserted into variable L. In step 132, n on-chip coordinates are randomly generated. The X coordinates of these generated on-chip coordinates are then inserted into variables RX to RAN. The Y coordinates are inserted into the variables RYE to RAN. In step 133, variable J is initialized. The value of variable J is the identification number of the layer in integrated circuits of multilayer construction. In step 134, variable J is incremented. In step 135, condition branching takes place depending on the magnitude relationship of variable J and variable L. If variable J is less than or equal to variable L, processing advances to step 136; otherwise, processing advances to step 139. In steps 136 to 138, processing is performed with respect to the layer corresponding to the value of variable J. In step 136, the relationship of the n data from coordinates RX, RYE to RAN, RAN to the circuit layout data is examined. The distance to a circuit pattern in the vicinity is calculated from the above coordinates, then the distance that can geometrically cause a short circuit of the circuit patterns is calculated for each coordinate RAN, RAN. The distance that can cause a short circuit of the circuit patterns is the distance that is larger than both the distance from the above coordinates to the nearest pattern and the distance from the above coordinate to the second nearest circuit pattern. In step 137, on-chip region division is performed. Thus, the chip is divided into P in the X direction and into Q in the Y direction. In step 138, the Kill Ratio DR (J, p, q) for each layer and for each region is calculated. Here, J represents the layer, p represents the X coordinate of the region obtained by the division into P, and q represents the Y coordinate of the region obtained by the division into Q.

Figure 8:
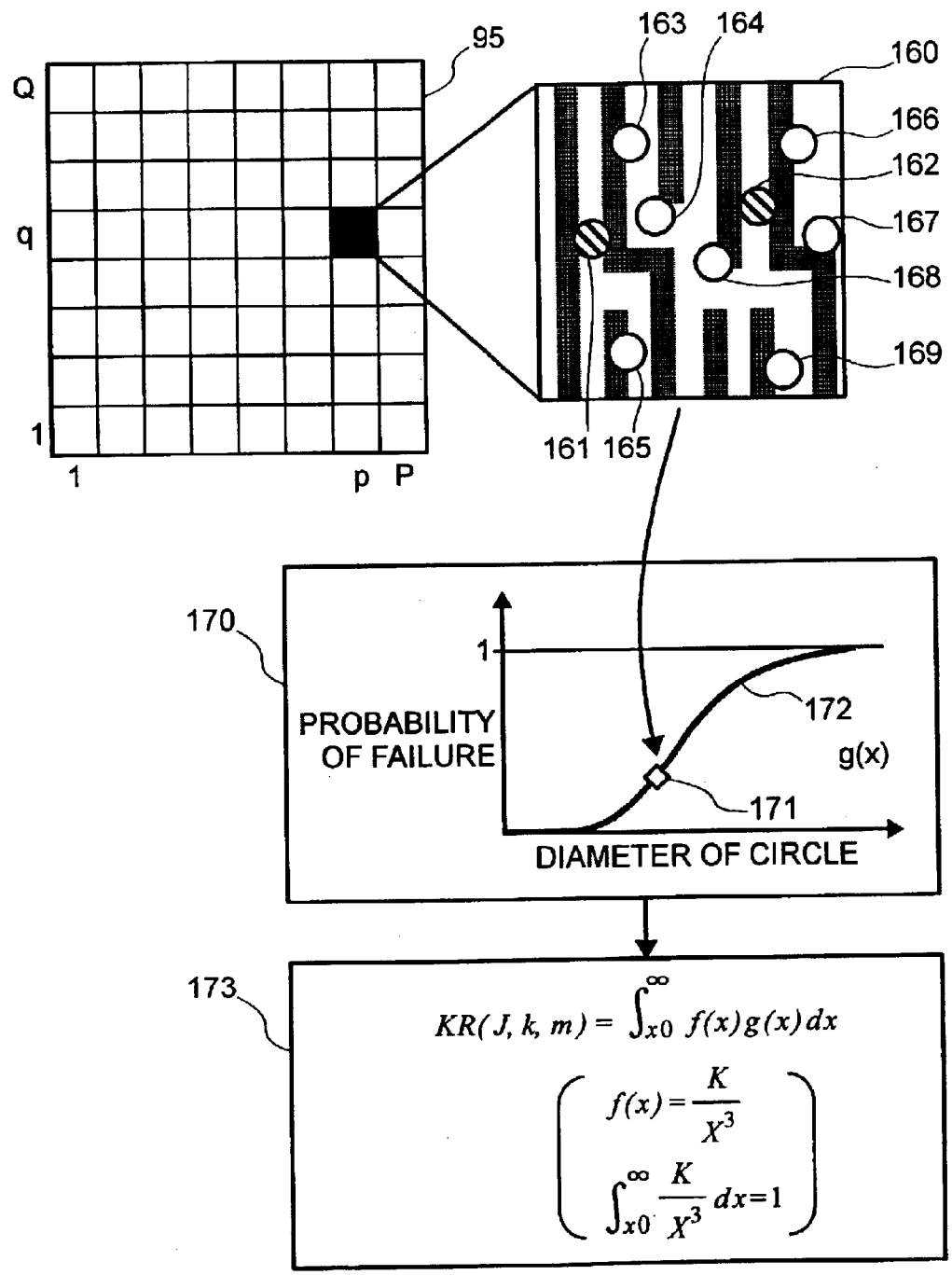
FIG. 8 is an example of a method for calculating sparse regions within a chip.

FIG. 8 illustrates steps 136 to 138. Element 95 represents the outer frame of the chip. The chip is divided into P in the transverse direction and is divided into Q in the longitudinal direction. The region shown in black is a divided region (p, q). Rectangle 160 shown in FIG. 8 is the divided region (p, q) at a larger scale. The circuit patterns are shown in gray. The centers of circles 161 to 169 are random coordinates generated in step 132. In this example, circle 161 and circle 162 indicated by shading cause short circuits. This means two of nine defects whose diameters are all same as the diameter shown in FIG. 8 cause short circuits. Point 171 on graph 170 is the result of plotting this "two out of nine" probability of failure on a graph. If the size of circles 161 to 169 is altered, curve 172 can be obtained. If (math 1) shown in frame 173 is calculated, taking this curve 172 as g(x) (where x is the diameter of the circles), the Kill Ratio of a divided region (p, q) of the layer corresponding to variable J can be calculated. It will be assumed that f(x) in (math 1) is a curve that can be expressed by (math 2) and that the coefficient k in (math 2) can be expressed by (math 3). Also, xi in (math 1) and (math 3) will be assumed to specify a minute value such as 0.1 micrometer. The method of calculating Kill Ratio that is indicated here applies the critical area analysis methods described in Laid-open Japanese Patent Application No. Sho. 48-40376, Laid-open Japanese Patent Application No. H. 8-162510 and the article "Modeling of Defects in Integrated Circuit Photolithographic Pattern" by C. H. Stapper published in the *IBM Journal of Research and Development*, No. 4, Volume 28, 1984.

$$KR(J, p, q) = \int_{x0}^{\infty} f(x)g(x)dx \qquad (1)$$

$$f(x) = \frac{k}{x^3} \qquad (2)$$

$$\int_{x0}^{\infty} \frac{K}{x^3} dx = 1 \qquad (3)$$

Although, in this example, a case where short circuits were geometrically generated was illustrated, there is no restriction to this and a case of disconnections could also be calculated. In FIG. 7, step 139 is executed if, at step 135, variable J exceeds the value of variable L. Specifically, step 139 is executed for all layers after steps 136 to 138 have been executed. In step 139, (math 4) is calculated from the Kill Ratio DR (J, p, q) for each divided region for each layer.

$$TKR(p, q) = 1 - \prod_{J=1}^{L} \left(1 - KR(J, p, q)\right) \qquad (4)$$

where (p, q) indicates the coordinates of a divided region.

In step 140, if the value of TKR (p, q) calculated by (math 4) for each divided region is smaller than a predetermined threshold value, it is concluded that the circuit patterns constitutes sparse regions and the patterns are therefore designated non-examination regions. If the value is above the threshold value, the region is designated as an inspection region. As a result, on-chip inspection regions and non-inspection regions of the integrated circuits can be determined.

Although, in this example (math 4) was employed as step 139, there is no restriction to this and, for example, instead of (math 4), (math 5) could be employed. According to the present invention, when the circuit patterns are dense in a region in one or more layers, the region in question is designated an inspection region; when the circuit patterns are sparse in a region through all the layers, the region is designated anon-inspection regions.

$$TKR(p, q)=max(KR(1, p, q), KR(2, p, q), KR(3, p, q), \ldots, KR(L,p,q)) \quad (5)$$

where max ( ) indicates a maximum value.

Figure 9:
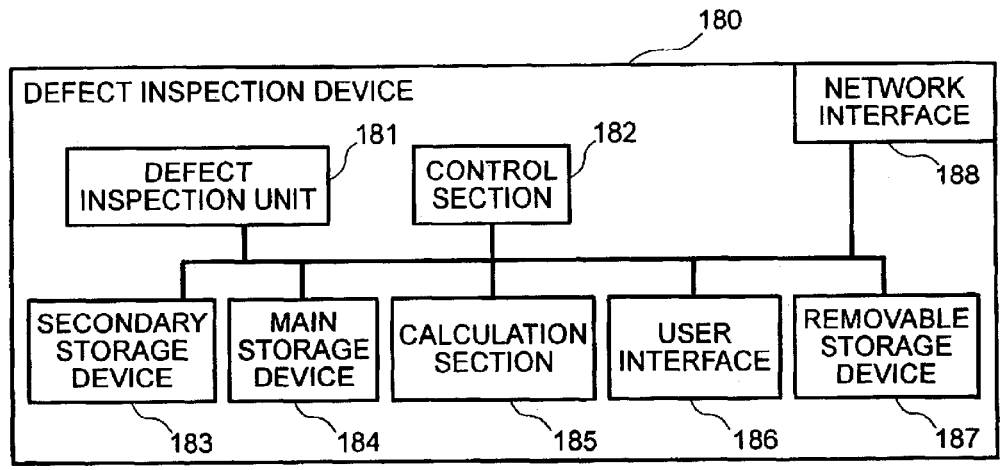
FIG. 9 is an example of a defect inspection device that executes a program.

FIG. 9 is an example of a defect inspection device for executing the present invention. Defect inspection device 180 includes a defect inspection unit 181, control section 182, secondary storage device 183, main storage device 184, calculation section 185, user interface 186, removable storage device 187 and network interface 188. Defect inspection unit 181 includes a stage that moves the wafer left and right and vertically and mechanically places the wafer in position, and lenses and detectors for illuminating the wafer with laser light for picking up images of defects on the wafer. Control section 182 controls the operation of defect inspection unit 181, secondary storage device 183, main storage device 184, calculation section 185, user interface 186, removable storage device 187 and network interface 188. Secondary storage device 183 is a storage medium such as a hard disk. A program according to the present invention is stored on secondary storage device 183. The circuit pattern conditions prepared in the program in accordance with the present invention also are stored on the secondary storage device. Main storage device 184 is a storage medium such as a random access memory. When the program of the present invention is executed, the program stored in secondary storage device 183 is read by main storage device 184. Calculation section 185 is a calculation processing device such as a microprocessors and performs calculations in accordance with the program that are read into main storage device 184. User interface 186 comprises an output device such as a display or printer and/or an input device such as a keyboard or mouse. This program is started up using the input device, and the graphical user interface shown in FIG. 2 is displayed on a display constituting an output device. Removable storage device 187 is a medium such as an optical disc or magneto-optical disc, and is employed for inputting CAD circuit layout data. Instead of the removable storage device 187, a network interface 188 can input CAD circuit layout data by connecting defect inspection device 180 to a network such as a local area network.

Figure 10:
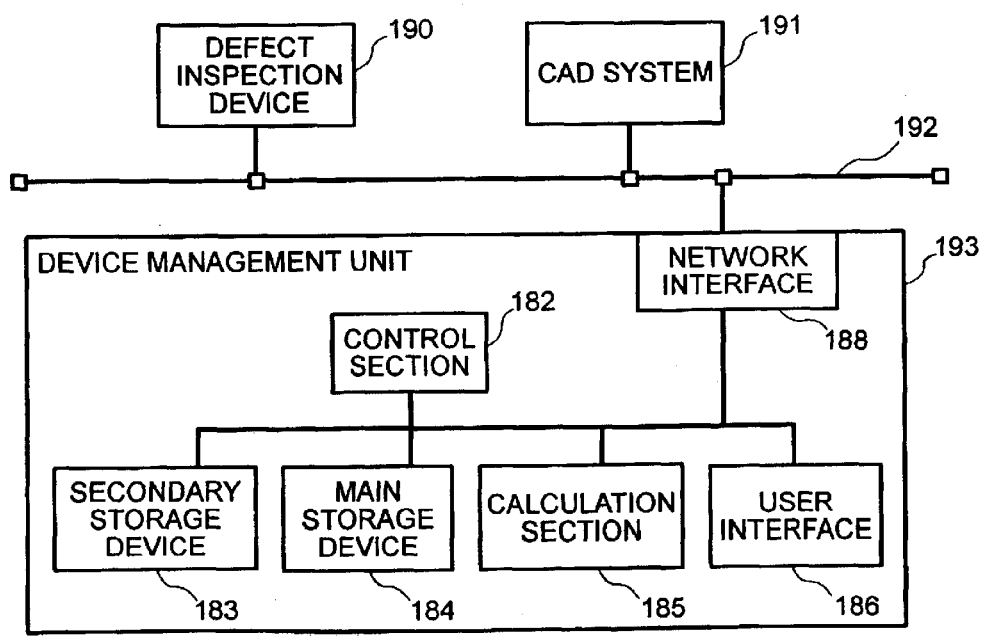
FIG. 10 is an example of an inspection system that executes a program.

FIG. 10 shows an example of an inspection system for executing the present invention. A program according to the present invention may be executed within a defect inspection device as in FIG. 9, or in a device management unit as in FIG. 10. A program according to the present invention may be executed in device management unit 193 by a computer separate from the defect inspection device. Defect inspection device 190 is connected to a local area network 192. Device management unit 193 also is connected to local area network 192. Device management unit 193, like defect inspection device 190 of FIG. 9, includes a control section 182, secondary storage device 183, main storage device 184, calculation section 185, user interface 186 and network interface 188. The program of the present invention is stored in secondary storage device 183. This program is executed by being read into main storage device 184. The results of execution of this program are stored in secondary storage device 183 and transmitted to defect inspection device 190 via network interface 188 and local area network 192.

The example described above illustrates a method of registering circuit pattern conditions. The method has the following processes: the coordinates of repeated pattern regions are extracted from circuit layout data constituting the output of a CAD system, and the regions are designated as cell comparison regions in the inspection device; the coordinates of regions in which the circuit patterns are sparse are extracted and the regions are designated as non-inspection regions; scribe line regions at the chip periphery are designated as non-inspection regions. Setting of the cell comparison regions, setting of the inspection regions and setting of the non-inspection regions can be achieved by executing programs designed for each setting; or each program can be executed independently.

As described above, a program is provided that is executed for setting circuit pattern conditions efficiently and with high precision The conditions are required to inspect defects such as particles or deformed patterns using a defect inspection device such as a patterned or an unpatterned wafer inspection device. By executing the program according to the present invention, the setting of coordinates of repeated pattern regions or the coordinates of non-inspection regions, can be achieved faster and more precisely than by conventional methods.

What is claimed is:

1. A program for setting inspection conditions that is executed for setting inspection conditions of an inspection device that detects the positions of particles or deformed patterns present in or on a subject of inspection, wherein the program executes:

circuit layout reading processing of reading circuit layout data formed on the subject of inspection, wherein the circuit layout data is the output data of a CAD system;

repeated pattern region coordinates extraction processing in which the coordinates of repeated pattern regions in the circuit layout are extracted from the circuit layout data that has thus been read in the circuit layout reading processing; and inspection region registration processing in which the coordinates of repeated pattern regions that have thus been extracted by the repeated pattern region coordinates extraction processing are registered as inspection regions of the inspection device.

2. The program for setting inspection conditions according to claim 1 wherein array sections are extracted from the circuit layout data in said repeated pattern region coordinates extraction processing.

3. The program for setting inspection conditions according to claim 1 wherein the same processing as in cell comparison inspection cell comparison inspection processing provided by the inspection device is executed with respect to the circuit layout data in said repeated pattern region coordinates extraction processing.

4. The program for setting inspection conditions according to claim 1 wherein, in order to execute said repeated pattern region coordinates extraction processing and said inspection region coordinates registration processing, a graphical user interface is provided, and repeated pattern regions are output to this graphical user interface.

5. A program for setting inspection conditions that is executed for setting inspection conditions of an inspection device that detects the position of particles or deformed patterns present in or on a subject of inspection, wherein the program executes:

circuit layout reading processing of reading circuit layout data formed on the subject of inspection, wherein the circuit layout data is the output data of a CAD system;

designated circuit block region coordinates extraction processing in which the coordinates of designated circuit block regions are extracted from the circuit layout data that has thus been read in the circuit layout reading processing; and inspection region registration processing in which the coordinates of circuit block regions that have thus been extracted by the designated circuit block region coordinates extraction processing are registered as inspection regions of the inspection device.

6. The program for setting inspection conditions according to claim 5 wherein, in order to execute said designated circuit block region coordinates extraction processing and said inspection region coordinates registration processing, a graphical user interface is provided, and circuit block regions are output to this graphical user interface.

7. A program for setting inspection conditions that is executed for setting inspection conditions of an inspection device that detects the position of particles or deformed patterns present in or on a subject of inspection, wherein the program executes:

circuit layout reading processing of reading circuit layout data formed on the subject of inspection, wherein the circuit layout data is the output data of a CAD system;

sparse region coordinates extraction processing in which the coordinates of regions where the circuit pattern is sparse are extracted from the circuit layout data that has thus been read in the circuit layout reading processing; and non-inspection region coordinates registration processing in which the coordinates of the sparse regions that have thus been extracted by the sparse region coordinates extraction processing are registered as non-inspection regions of the inspection device.

8. The program for setting inspection conditions according to claim 7 wherein, in said sparse region coordinates extraction processing, the probability of occurrence of short-circuiting or disconnection is calculated with respect to the circuit layout data and the coordinates of regions where the probability of occurrence of short-circuiting or disconnection has a value smaller than the threshold value which is given beforehand are extracted.

9. The program for setting inspection conditions according to claim 7 wherein, in said sparse region coordinates extraction processing, the density of the circuit patterns are calculated with respect to the circuit layout data and the coordinates of regions where the density is less than a previously given value are extracted.

10. The program for setting inspection conditions according to claim 7 wherein, in said sparse region coordinates extraction processing, the coordinates of scribe line regions between one chip and another chip of the integrated circuits are extracted as sparse regions.

11. The program for setting inspection conditions according to claim 7 wherein, in order to execute said sparse region coordinates extraction processing and said non-inspection region coordinates registration processing, a graphical user interface is provided, and sparse regions are output to this graphical user interface.

12. A program for setting inspection conditions that is executed for setting inspection conditions of an inspection device that detects the position of particles or deformed patterns present in or on a subject of inspection, wherein the program executes:

circuit layout reading processing of reading circuit layout data formed on the subject of inspection;

sparse region coordinates extraction processing in which the coordinates of regions where the circuit pattern is sparse are extracted from the circuit layout data that has thus been read in the circuit layout reading processing; and non-inspection region coordinates registration processing in which the coordinates of the sparse regions that have thus been extracted by the sparse region coordinates extraction processing are registered as non-inspection regions of the inspection device, wherein, in said sparse region coordinates extraction processing, the probability of occurrence of short-circuiting or disconnection is calculated with respect to the circuit layout data and the coordinates of regions where the probability of occurrence of short-circuiting or disconnection has a value smaller than the threshold value which is given beforehand are extracted.

13. A program for setting inspection conditions that is executed for setting inspection conditions of an inspection device that detects the position of particles or deformed patterns present in or on a subject of inspection, wherein the program executes:

circuit layout reading processing of reading circuit layout data formed on the subject of inspection;

sparse region coordinates extraction processing in which the coordinates of regions where the circuit pattern is sparse are extracted from the circuit layout data that has thus been read in the circuit layout reading processing; and non-inspection region coordinates registration processing in which the coordinates of the sparse regions that have thus been extracted by the sparse region coordinates extraction processing are registered as non-inspection regions of the inspection device, wherein, in said sparse region coordinates extraction processing, the density of the circuit patterns are calculated with respect to the circuit layout data and the coordinates of regions where the density is less than a previously given value are extracted.

14. A program for setting inspection conditions that is executed for setting inspection conditions of an inspection device that detects the position of particles or deformed patterns present in or on a subject of inspection, wherein the program executes:

circuit layout reading processing of reading circuit layout data formed on the subject of inspection;

sparse region coordinates extraction processing in which the coordinates of regions where the circuit pattern is sparse are extracted from the circuit layout data that has thus been read in the circuit layout reading processing; and non-inspection region coordinates registration processing in which the coordinates of the sparse regions that have thus been extracted by the sparse region coordinates extraction processing are registered as non-inspection regions of the inspection device, wherein, in said sparse region coordinates extraction processing, the coordinates of scribe line regions between one chip and another chip of the integrated circuits are extracted as sparse regions.

* * * * *